United States Patent [19]

Updike

[11] 3,970,429
[45] July 20, 1976

[54] METHOD FOR IMMUNOLOGICAL DETERMINATIONS

[75] Inventor: Stuart J. Updike, Madison, Wis.

[73] Assignee: Wisconsin Alumni Research Foundation, Madison, Wis.

[22] Filed: Jan. 28, 1974

[21] Appl. No.: 437,135

Related U.S. Application Data

[63] Continuation-in-part of Ser. No. 356,092, May 1, 1973.

[52] U.S. Cl................................ 23/230.6; 424/1.5
[51] Int. Cl.²........................................ G01N 31/06
[58] Field of Search............ 23/230 B, 259, 230.6; 424/1, 12, 1.5; 252/316; 210/31 C, 504; 260/80.3 N

[56] References Cited
UNITED STATES PATENTS

| | | | |
|---|---|---|---|
| 3,616,936 | 11/1971 | Johansson et al.................. | 210/504 |
| 3,728,290 | 4/1973 | Johansson et al.................. | 260/80.3 N X |
| 3,793,445 | 2/1974 | Updike et al....................... | 424/12 |

OTHER PUBLICATIONS

Clin. Chem., v. 19 (12), pp. 1339–1344, (1973), Updike et al.

Chem. Abstr., v. 73: 127610m (1970).
Chem. Abstr., v. 74: 123000k (1971).
Chem. Abstr., v. 75: 33018p (1971).

*Primary Examiner*—Joseph Scovronek
*Assistant Examiner*—Timothy W. Hagan
*Attorney, Agent, or Firm*—McDougall, Hersh & Scott

[57] ABSTRACT

A method for immunological determinations in which use is made of a volume of a hydrophilic, insoluble, porous gel particles having binding proteins entrapped therein, and in which a fluid to be tested is introduced into the volume of gel particles whereby some of the binding sites are occupied followed by exposure of the gel particles to radio active tagged material followed by measurement of the radio activity of the unbound or bound tagged material. The binding proteins in the gel particles are returned to their original state for reuse by treatment with acidic medium to effect detachment of the bound material followed by washing to effect removal of the unbound material, and then drying.

13 Claims, 1 Drawing Figure

U.S. Patent    July 20, 1976    3,970,429
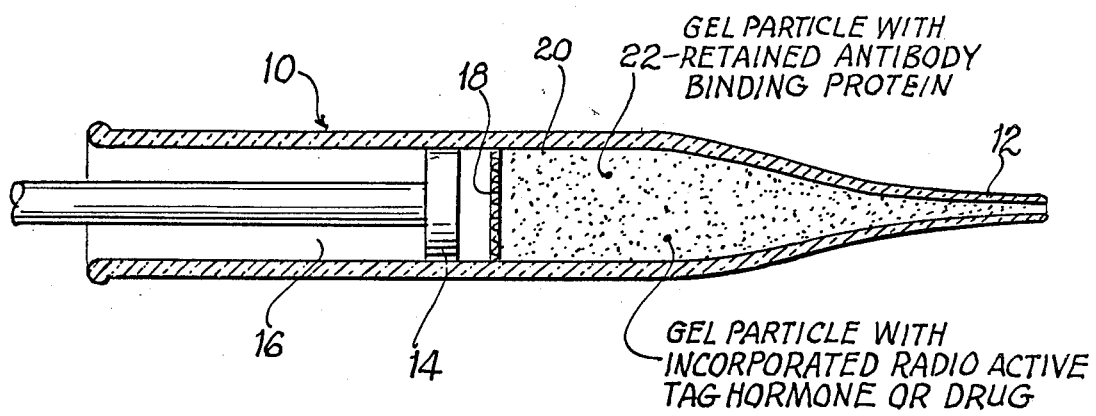

METHOD FOR IMMUNOLOGICAL DETERMINATIONS

The invention described herein was made in the course of work under a grant or award from the Department of Health, Education, and Welfare.

This is a continuation-in-part of my copending application Ser. No. 356,092, filed May 1, 1973, entitled "Device and Method for Sample Applications by Water Regain of a Gel".

This invention relates to clinical techniques for immunological determinations and more particularly to radioimmunoassay by manual and preferably by automated technique.

In the aforementioned copending application and in the copending application Ser. No. 33,098, filed Apr. 29, 1970, now U.S. Pat. No. 3,793,445 entitled "Reagent for Immunological Determinations", description is made of a device and technique for immunological determinations of a fluid system in which use is made of a measured volume of dried, insoluble, yet highly hydrophilic gel particles in which there are entrapped one or more binding proteins or combinations of binding proteins and radioactive tag material. The dry gel particles are characterized by pores of a size that permit entry of low molecular weight compounds into the intragel volume but insufficient to permit entry of large molecular weight components which remain in the extra gel volume, thereby to achieve a desirable fractionation which excludes high molecular weight interferences otherwise present to interfere with blood or serum assays.

Application of liquid sample to the measured volume of dry gel particles is determined by water regain of the gel thereby to provide a pipetless method of sample application based on use of highly reproducible dry-volume aliquots of the dried or lyophilized gel particles.

The dry gel particles can be preloaded with radioactive tagged hormone and standard hormone either during preparation of the dry gel particles, or by after treatment of the dry gel particles previously provided with the entrapped antibody.

The dry antibody-gel reagent is stable under widely diversified atmospheric conditions to enable storage over long periods of time without deviation or loss in binding activity. Thus, there is described a radioimmunoassay system which provides for automatic exclusion of high molecular weight interferences; elimination of the need to pipet or centrifuge the sample to be tested; long term stability of binding reagents stored under ambient conditions; and a reliable and accurate method of assay which has been successfully applied to the assay of angiotensin I and insulin.

The aforementioned copending applications are addressed to an assay system and device which is characterized by manual operation in a single use, with the device being discarded after the assay has been completed. However, it is desirable and it is an object of this invention to provide a system which is capable of automation for multiple use without loss in binding activity of the antibody gel particles thereby to afford reproducible results which makes the system for radioimmunoassay much more attractive, at least from the standpoint of cost, time, inventory and results.

Proteins having a binding capacity for certain specific smaller molecules and which can be readily immobilized in the polymer gel are illustrated by various protein globulins and antibodies.

Gel systems having such globulins or antibodies entrapped therein can be used effectively for analyzing for a variety of antigens or haptenes, such as drugs, polypeptide hormones and steroid hormones. Antigens and haptenes susceptible of being assayed in a system of the type described include, for example, angiotensin, insulin, growth hormone, gonadotropic hormone, parathyroid hormone, glucagon, cortisol, protoglandin, corticosteroids, cyclic fatty acid hormones and estrogens, and drugs such as digoxin, thyrosin, morphene, digitalis, and the like. By way of example, specific corticosteroid binding globulins, immobilized by entrapment in the gel system, permit assay of corticosteroid hormones in addition to the many polypeptide hormones. 7S gamma-globulin (150,000 m.w.) can be used to assay for angiotension (1,000 m.w.).

BRIEF DESCRIPTION OF THE DRAWING

The FIGURE shows a sectional view of a device with which to practice the method of the invention.

The invention will hereinafter be described in greater detail by reference to a specific example.

EXAMPLE 1

A gel, in which dilute anti-angiotensin immune serum containing 7S gamma globulin (m.w. 150,000) is entrapped in a gel matrix having a pore size to enable diffusion of angiotensin (m.w. 1,000) for assay may be prepared as follows:

8 grams of acrylamide and 1 gram of N,N'-methylenebis-acrylamide is dissolved to a final volume of 36 ml in sodium phosphate buffer solution (0.1 M, pH 7.4) containing a suitable dilution of antiserum. To the resulting solution 0.1 ml of a suspension of 100 mg of riboflavin in 20 ml of distilled water and 0.02 ml of N,N,N',N-tetramethyl-ethylenediamine is added, followed by 0.2 mg of sodium hydrosulfite. The mixture, in a suitable vessel, is stoppered and agitated and then is exposed to light from an ordinary tungsten light bulb to induce polymerization. Polymerization is complete in 5–15 minutes. The reaction vessel is continuously chilled in an ice water bath, as needed, to prevent the heat generated by the exothermic polymerization reaction from adversely affecting the binding protein.

The antibody gel is fragmented by pushing through a No. 40 mesh brass screen. The gel particles are collected on a No. 60 mesh screen and washed with 5 liters of distilled-deionized water. The gel particles sediment rapidly and are stiff enough to tolerate moderate flow rates (0.5 to 2.0 ml/min) in a chromatographic column without plugging. After sieving, the gel particles are equiliberated with 0.1 M pH 7.4 phosphate buffer. The gel particles are now ready for the drying procedure.

Two fundamentally different drying procedures have been employed including (1) lyophilization and (2) dehydration in acetone, ethanol, or other low boiling alcohol, followed by air drying. Neither method was associated with loss of antibody activity. However, ethanolic dehydration is preferred because of its simplicity and rapidity of drying. For this purpose, the gel particles were suspended in 5 volumes of 95% ethanol and allowed to settle. The supernatant solution was discarded and the ethanol treatment repeated one or more times. The ethanol dehydrated gel particles were then allowed to dry in room air by spreading on a nylon net.

Storage stability has been demonstrated by hermetically sealing the lyophilized gel particles, with the entrapped antibody activity, at temperatures of 37°C, 25°C, 4°C and −20°C for over two years without detectable loss of antibody activity when the entrapped protein is in the form of anti-insulin introduced by the way of antibody sera for the anti-angiotensin in the described example. Dried gel particles containing anti-angiotensin antibody prepared in accordance with this example has also demonstrated storage stability, without loss of antibody activity for over six months. As indicated above, rabbit antisera for use against angiotensin I and guinea pig antisera for use against insulin can be substituted for the antisera in producing the antibody gel particles of this example.

EXAMPLE 2

Evaluation device:

In its simplest form, an evaluation device for radioimmunoassay, as described in the aforementioned copending application, is illustrated in the form of a syringe 10, such as a 1 ml tuberculin syringe, having a syringe needle 12 at one end and a plunger 14 operative in an elongate barrel at the other end for drawing fluid for unidirectional flow through the needle 12 into the body portion 16 of the syringe in response to the generation of volume conditions upon withdrawal of the plunger.

Adjacent the needle end portion, the syringe is subdivided by a porous barrier 18 into a calibrated portion 20 packed with a column of prescribed volume of the dry gel particles of Example 1, while the plunger or other withdrawal means communicates with the portion beyond the barrier 18.

In the described device, the barrier is in the form of a nylon fabric or net having openings insufficient to permit passage of the gel particles. In the illustrated modification, 33 mg of dry gel particles are packed in the volume of 0.14 ml enclosed by the porous barrier made up of about two-thirds intra gel volume and about one-third extra gel volume, with the dry gel particles having a water regain of 100 mg water per 33 mg gel particles.

EXAMPLE 3

Method of use:

In manual use, the needle 10 is inserted in the sample (serum, plasma or whole blood drawn directly from a vein) and the plunger is pulled back to draw some of the liquid sample into the syringe 10 in an amount to at least fill the volume 20 below the barrier 18 and preferably in an amount to at least cover the net.

As the sample is drawn into the syringe, the highly hydrophilic gel particles 22 absorb a predictable and reproducible portion of low molecular weight component in the sample by rehydration. To prevent coagulation, when testing fresh whole blood or plasma, it is desirable to incorporate a coagulant into the gel recipe from which the dry gel particles are formed.

The size of the sample that is taken up by the particles depends upon the water regain value of the gel as well as the amount of particles present in the column, measured by weight or by volume. As a result, sample size can automatically be controlled by the amount and water regain value of the dried gel particles thereby to make the test reproducible and accurate, independent of the amount of liquid sample that is drawn into the syringe.

After the sample has been drawn into the syringe, the void volume (extra gel volume of the miniature-syringe chromatographic column) is flushed out, as with a buffer solution, such as a 0.1 M phosphate buffer or any other physiological solution. The flushing liquid should be employed in an amount corresponding to at least one void or extra gel volume but it is preferred to make use of more than one and preferably two to five void volumes in order to insure the removal of sample component otherwise remaining in the extra gel volume. The low molecular weight polypeptide hormone (or other antigen or haptene) remains substantially entrapped within the intra gel space during this rapid column wash step for removing high molecular weight interference. Thus high molecular weight interferences are removed with the wash solution used to flush the column of gel particles.

After the flushing step, a competing radioactive "tag" hormone of known concentration is drawn into the syringe in an amount to at least fill the void volume and preferably in an amount greater than one void volume.

The unit is then incubated for a specific period of time, which may range from 30 seconds to 30 hours, at room temperature. It is not necessary for the radio competitive binding assay to go completely to equilibrium before final separation of the bound from the free radioactivity.

Thereafter, a buffered wash solution, which may be the same as that used to flush the column in the previous step, is passed through the column. This operates to separate unbound hormones from bound hormones. The column is flushed with sufficient volume for a length of time substantially to complete the separation step. The total amount of tagged radioactive hormone used will equal the bound plus the unbound. The radioactivity bound to the binding sites in the column can be measured directly or it can be determined indirectly by measuring the radioactivity of the wash solution. Use can be made of standard values sufficient to construct a standard working curve having the per cent bound as the abscissa and the log scale of the standard as the base, whereby the unknown in the sample can be read directly from the curve, in accordance with the standard procedures of current radioimmunoassay.

The described technique and materials are capable of a number of modifications and ramifications.

The formulation of the gel of which the particles are formed is not significant since use can be made of any gel forming material which is capable of being reduced into porous, insoluble, highly hydrophilic particles of controlled pore size. Thus, other highly hydrophilic, insoluble gels capable of the desired pore size and drying or lyophilization can be used but it is preferred to make use of the polyacrylamide gels of the type described wherein an acrylamide monomer and cross linking agent are combined with sufficient cross linking agent to stabilize the pore size and support the monomer not only to provide the desired pore size but to give the gel the density desired for rapid sedimentation in particulate form and to provide sufficient rigidity to the gel particles.

As described in the aforementioned application, the ratio of one part by weight of cross linking agent to 4 to 10 parts by weight monomer is sufficient to give a gel having a total gel polymer concentration in the range of 12–35%.

The binding globulin, antibody or protein entrapped within the dry gel particles can be varied, depending upon the hormone, drug or other material to be assayed, such as angiotensin, insulin, growth hormone, gonadotropic hormone, parathyroid hormone, cortisol, digoxin, digitalis or thyroxin.

The water regain value of the gel particles determines how much sample reaches the antibody binding protein contained in the intra gel compartment. The water regain of the gel will depend somewhat on the per cent polymer and per cent cross linking agent and more particularly on the thoroughness of the drying process. The gel reagents of the type described can be dried so that water regain will not change under the conditions of temperature and humidity used in storage. Other degrees of dryness and water regain can be used, but are not convenient, because of changes in hydration that occur with changes in storage temperature and humidity. The particle size as well as the form and shape of the dry gel particles can be varied depending upon the size and shape of the test device.

Instead of a syringe, other containers can be employed in which a known volume or weight of dry gel particles can be retained and through which the liquid sample, flush solution and tag solution can be transported for engagement with the gel particles in the amounts previously described. In the event that a device is used in which the gel particles are retained as a column in an intermediate section of known volume, then barriers such as a nylon net should be provided at opposite ends to confine the particles into the chromatographic column while enabling the various fluids to pass therethrough into and out of the column of particles.

The porous barrier functions automatically to separate bound from unbound radioactivity which occurs during the flushing of the column. This porous structure functions also an an anticonvection barrier, which discourages mixing of any solution sequestered outside the gel particle compartment.

Since the volume of gel particles is known and the water regain is constant, the amount of sample taken up by the gel particles will be the same independent of the size of the sample or the amount introduced into the test unit. The same applies with respect to the fluid solution used to flush the particles for removal of material in the extra gel volume and the amount of radioactive tag material to which the gel particles are ultimately exposed. Thus many of the steps critical to prior immunoassays have been eliminated with equal or greater reproducibility and accuracy of test results. Since the antibody is insolubilized and immobilized within the gel particles, conventional centrifugation and washing steps, normally employed in current procedures, can be eliminated in their entirety in the preparation and use of a test unit of the type described.

Similarly, since the unknown and tag material taken up depends on such known values as volume and water regain, the critical steps of pipetting and the numerous errors associated therewith are eliminated thereby to increase the accuracy of the analysis.

By immobilizing the antibody binding reagent in the gel, the centrifugation step of conventional RIA can be eliminated. Furthermore, by engaging the antibody binding protein in a gel polymer matrix, high molecular weight interference of RIA can be excluded. Such high molecular weight interferences which are found in some but not all biological samples, are of at least two types, namely, (1) proteolytic enzymes, which can degrade polypeptide hormone, and (2) endogenous antibody, which can bind polypeptide hormone. Endogenous antibody that binds insulin is frequently found in patients treated with injections of bovine or porcine insulin. These high weight molecular interferences are too large to penetrate into the polymer matrix of the gel particles and are sequestered in the extra gel space, where they can be removed by washing the gel column.

The device which has heretofore been described, and described in the copending application, has been manually applied for single assays, after which the device is discarded. It would, of course, be desirable to be able to make multiple use of the device, without loss of binding activity, and it would be still more desirable to be able to automate the operation for multiple use thereby to effect considerable savings in time and materials, as well as reproducibility of the results.

It has been found, in accordance with the practice of this invention, that the binding sites of the antibody gel particles in the chromatographic column of the test device can be returned to their original state to enable re-use as a test device, without loss of binding site, and that this can be achieved again and again in a simple and efficient manner for either manual or automated radioimmunoassay systems.

Unbound radioactivity can be washed from the column, in the manner previously described, with a variety of physiological solutions at neutral pH for separation of unbound radioactivity and unbound hormones from the system. Bound radioactivity can be detached from the binding sites to enable elution from the antibody gel particles in the column by an acid or hyperthermic wash solution.

The unbound radioactivity and hormone washed from the column or the bound radioactivity eluted from the antibody gel particles can be made the subject of analysis, as by gamma or liquid scintillation type detectors, to arrive at the assay value for the previous sample.

Following elution of the bound radioactivity, the column of gel particles is washed with a buffer for removal of the acid or hyperthermic reagents. This is followed by washing with an organic solvent which is at least partially miscible with water and which is highly volatile and which forms a constant boiling mixture with water to effect removal of the buffer and to enable rapid dehydration and collapse of the antibody gel particles. Upon evaporation of the organic solvent these gel particles have been returned to their original dry state. Collapse of the gel particles, which occurs with solvent drying, is preferred because it prevents entrapment of large amounts of air which effect reproducibility of the quantity of sample or water regain and/or is released as tiny bubbles on rehydration.

For detachment of the bound radioactivity and bound hormones from the binding sites of the antibody gel particles in the column, it is preferred to make use of an aqueous acidic medium having a pH of less than 2.5 and preferably an aqueous solution of hydrochloric acid. The acidic solution is introduced into the gel column in an amount corresponding to at least one gel volume and preferably more than one gel volume but less than three.

Removal of the acidic medium with the detached radioactivity and hormones is effected by washing with a buffer solution, such as an 0.1 M phosphate buffer having a pH of about 7.4 but other suitable buffers can be used as previously described. The amount of buffer passed through the column should be sufficient to rinse the acid from the column of gel particles, usually one to five volumes will be sufficient.

The organic solvent is employed primarily to effect removal of aqueous medium and to permit rapid drying and collapse of the gel particles in the column. For this purpose, it is desirable to make use of an organic solvent which does not denature the binding activity of the entrapped antibody and which forms a constant boiling mixture with aqueous medium to effect water removal and in which the organic solvent is highly volatile to facilitate rapid removal and permit rapid drying of the gel particles. Representative of suitable organic solvents are acetone, methyl alcohol, ethyl alcohol, low boiling esters, and the like.

Solvent removal and accelerated drying is effected by passing air through the column at ambient temperature or at a temperature slightly above ambient but below the temperature which would destroy any of the antibody binding sites. The stream of drying air accelerates volatilization of the organic solvent for rapid and complete removal.

The thus regenerated antibody gel particles in the column are returned to their original state including collapsed structure for re-use of the test device without the need for any recalibration.

It will be apparent from the foregoing description that, in the regeneration as well as in the use of the device, the materials are caused to flow through the device in one direction. Such column-chromatographic, unidirectional flowing stream configuration of analysis and regeneration enables complete automation of the use and regeneration of the device merely by the addition of a precision syringe or proportionating pump operatively connected with the ingoing end of the device to force the passage of the various materials in the desired volumes therethrough; a detection means communicating with the outgoing end of the device to test for unbound radioactivity or bound radioactivity in the materials that are eluted from the column; and a processor-controller for sequencing the materials for flow through the device.

An automated system of the type described provides for highly reproducible applications of samples, reagents, wash solutions, solvents and air to the column of antibody gel particles. The ability to exclude high molecular weight interferences and to work with highly stable pre-packed antibody gel reagent is advantageous for both manual and automated approaches. Gel antibody RIA does not require dilution of plasma to reduce or eliminate high molecular weight interferences. Thus reaction kinetics need not be slowed by reason of dilution in the system.

Manual methods of radioimmunoassay (RIA) have generally called for incubation of several hours in order for the system to reach equilibrium. However, in the described automated system, it is no longer necessary to reach equilibrium before carrying out the separation of bound from unbound hormone. Response times of 5 to 10 minutes are achievable with automation with a test device of the type described.

I claim:

1. In a method for immunological determinations in which use is made of a volume of hydrophilic, insoluble, porous polyacrylamide gel particles containing proteins having binding sites, introducing a fluid to be tested into the volume whereby some of the binding sites become occupied, exposing the gel particles to radioactive tagged material, and then measuring the radioactivity of the unbound tagged material or bound tagged material, the improvement of regenerating the volume of gel particles for re-use in subsequent immunological determinations comprising the steps of exposing the volume of gel particles to acidic wash solution to effect detachment of material bound to the binding sites of the protein, washing the volume of gel particles to elute the unbonded material, washing the volume of gel particles with a highly volatile organic liquid which has an affinity for water for removal of aqueous medium, and then removing the organic liquid to return the gel particles to the dried and collapsed state for subsequent use in an immunological determination.

2. The method as claimed in claim 1 in which the acidic material is an aqueous solution having a pH below 2.5.

3. The method as claimed in claim 2 in which the acidic medium is a solution of hydrochloric acid.

4. The method as claimed in claim 1 in which the gel particles treated to effect unbonding of the materials are washed with an aqueous buffer solution.

5. The method as claimed in claim 4 in which the buffer solution is a phosphate buffer.

6. The method as claimed in claim 4 in which the wash solution is introduced into the volume in an amount of at least one volume.

7. The method as claimed in claim 1 in which the highly volatile organic liquid is selected from the group consisting of an alcohol, acetone or ester.

8. The method as claimed in claim 7 in which the organic liquid is an organic solvent introduced in an amount of at least one volume.

9. The method as claimed in claim 1 in which the organic liquid is removed by passing air through the volume of gel particles to effect removal by evaporation of the organic liquid.

10. The method as claimed in claim 1 in which the dry gel particles are arranged in the form of a column and in which the materials are passed through the column in one direction for unidirectional flow.

11. The method as claimed in claim 10 in which the materials are passed through the column from an inlet at one end through an outlet at the other.

12. The method as claimed in claim 1 which includes the step of detecting the amount of radioactivity in the unbonded material eluted from the column or the bound material eluted from the column.

13. The method as claimed in claim 1 in which the gel particles are subjected to sequential regeneration by unidirectional flow of materials therethrough.

* * * * *

UNITED STATES PATENT OFFICE
CERTIFICATE OF CORRECTION

Patent No. 3,970,429           Dated   July 20, 1976

Inventor(s) Stuart J. Updike

It is certified that error appears in the above-identified patent and that said Letters Patent are hereby corrected as shown below:

Claim 4, line 2, cancel "unbonding" and substitute
--- detachment ---

Signed and Sealed this

Twenty-sixth Day of October 1976

[SEAL]

Attest:

RUTH C. MASON
*Attesting Officer*

C. MARSHALL DANN
*Commissioner of Patents and Trademarks*